United States Patent [19]

Chase

[11] 3,996,209

[45] Dec. 7, 1976

[54] PROCESS FOR PREPARING BENZODIAZEPINES

[75] Inventor: George Oswald Chase, Hawthorne, N.J.

[73] Assignee: Hoffmann-La Roche Inc., Nutley, N.J.

[22] Filed: June 2, 1975

[21] Appl. No.: 583,234

Related U.S. Application Data

[63] Continuation of Ser. No. 359,814, May 14, 1973, abandoned, which is a continuation-in-part of Ser. No. 282,217, Aug. 21, 1972, abandoned.

[52] U.S. Cl. .................. 260/239.3 D; 260/295 Q; 260/295 S; 260/295 R; 260/562 N; 260/999
[51] Int. Cl.$^2$ ............ C07D 243/28; C07D/401/04
[58] Field of Search ............................ 260/239.3 D

[56] References Cited

UNITED STATES PATENTS 3,886,141   5/1975   Chase .................. 260/239.3 D

FOREIGN PATENTS OR APPLICATIONS 7,001,765   4/1971   Netherlands ............... 260/239.3 D

OTHER PUBLICATIONS

Blazevic et al. I. "J. Het. Chem." vol. 7 pp. 1173–1174 (1970).
Blazevic et al. II "J. Het. Chem." vol. 9 pp. 531–537 (1972).

*Primary Examiner*—Henry R. Jiles
*Assistant Examiner*—Robert T. Bond
*Attorney, Agent, or Firm*—Samuel L. Welt; Bernard S. Leon

[57] ABSTRACT

1,4-Benzodiazepin-2-ones are prepared via the reaction of a haloacetamidophenyl ketone with hexamethylenetetramine in the presence of ammonia. The 1,4-benzodiazepin-2-ones so prepared are known compounds useful as muscle relaxant and anti-convulsant agents.

16 Claims, No Drawings

PROCESS FOR PREPARING BENZODIAZEPINES

This is a continuation of application Ser. No. 359,814 filed May 14, 1973, which in turn is a continuation-in-part of application Ser. No. 282,217 filed Aug. 21, 1972. Both applications are now abandoned.

PERTINENT PRIOR ART

In the *Journal of Heterocyclic Chemistry*, 7, 1173 (1970) the preparation of 5-phenyl-1,4-benzodiazepines utilizing hexamethylenetetramine is disclosed.

DETAILED DESCRIPTION OF THE INVENTION

The present invention provides the art with a procedure for the preparation of compounds of the formula

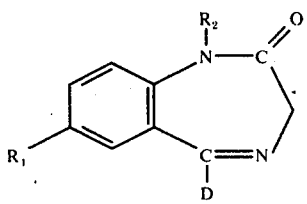

wherein D is selected from the group consisting of

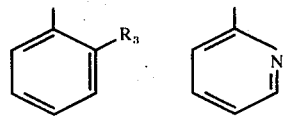

$R_1$ is selected from the group consisting of hydrogen, halogen, nitro and trifluoromethyl, $R_2$ is selected from the group consisting of hydrogen and lower alkyl and $R_3$ is selected from the group consisting of hydrogen and halogen
which comprises reacting a compound of the formula

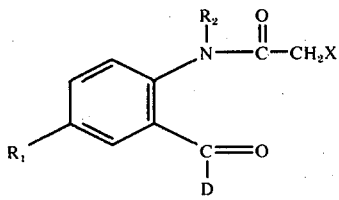

wherein D, $R_1$ and $R_2$ are as above and X is selected from the group consisting of chlorine, bromine and iodine (preferably chlorine) with hexamethylenetetramine, the improvement residing in the performance of the reaction in the presence of ammonia.

By the term "lower alkyl" as utilized hence herein, there is intended straight or branched chain aliphatic hydrocarbon groups such as methyl, ethyl, propyl, butyl and the like. When $R_2$ is lower alkyl, it is preferably methyl. By the term "halogen" as utilized herein, all four forms thereof are contemplated, i.e. chlorine, bromine, fluorine and iodine, unless otherwise specified. When $R_1$ is halogen, preferred are the halogens, chlorine or bromine, with chlorine being especially preferred. When $R_3$ is halogen, preferred are the halogens, chlorine and fluorine, with fluorine being especially preferred.

Preferred compounds whose preparation is effected by the procedure described herein include:
 7-chloro-1,3-dihydro-5-phenyl- 2H-1,4-benzodiazepin-2-one;
 7-chloro-5-(2-chlorophenyl)-1,3-dihydro-2H-1,4-benzodiazepin-2-one;
 1,3-dihydro-7-nitro-5-phenyl- 2H-1,4-benzodiazepin-2-one;
 7-chloro-1,3-dihydro-5-(2-fluorophenyl)-2H-1,4-benzodiazepin-2-one;
 1,3-dihydro-7-nitro-5-(2-fluorophenyl)-2H-1,4-benzodiazepin-2-one;
 5-(2-chlorophenyl)-1,3-dihydro-7-nitro-2H-1,4-benzodiazepin-2-one;
 7-bromo-1,3-dihydro-5-(2-pyridyl)-2H-1,4-benzodiazepin-2-one
and the 1-methyl derivatives of these compounds.

The prior art discloses the preparation of benzodiazepines of the formula I utilizing hexamethylenetetramine and a compound of the formula II. Such prior art procedures do result in good yields when certain starting materials of the formula II are utilized, e.g. when in the formula II $R_2$ is lower alkyl. However, for example, when $R_2$ is hydrogen consistently good yields are not obtained.

It has been discovered by the present applicant, that if ammonia is present in the reaction zone during the reaction of a compound of the formula II with hexamethylenetetramine, better yields of the compounds of the formula I result generally when compared with the procedure disclosed in the *Journal of Heterocyclic Chemistry*, 7, 1173 referred to above regardless of the character of the starting material utilized. Hence, the present invention improves upon the prior art as reflected in the aforementioned article by providing a general approach to the class of compound illustrated in formula I utilizing a compound of the formula II and hexamethylenetetramine which is simple and facile and which results in higher yields than with the aforementioned prior art process. Furthermore, a compound of the formula I of good purity is obtained when following the techniques described herein.

When proceeding from the compound of the formula II to the corresponding compound of the formula I utilizing hexamethylenetetramine, the reaction is effected in the presence of any inert organic solvent, which is suitable for the purposes of the present invention. Among the many such inert organic solvents so suitable, there can be included lower alkanols, such as methanol, ethanol, n-butanol and the like, dimethylformamide and similar inert organic solvents as well as aqueous mixtures of these, e.g. aqueous ethanol (95%), aqueous butanol. All this is required of the solvent is that the starting materials be soluble therein and that the solvent does not interfere with the ensuing reaction. Preferred are lower alkanols, such as methanol or ethanol. Furthermore, the character of the solvent should be such that it possesses the propensity to solubilize ammonia in the form that it enters the reaction zone.

While temperature and pressure are not critical to a successful performance of the process described herein, it is preferred to perform the reaction at a temperature of from about room temperature to about the reflux temperature of the reaction medium. Most preferably, elevated temperatures are utilized, most suitably, a temperature at about the reflux temperature of the reaction medium. Furthermore, in one embodiment, the reaction is performed under pressure to increase the concentration of ammonia present in the reaction zone.

Preferably, the ammonia is added to the reaction medium in such amounts as to saturate the inert organic solvent. As noted above, it is preferable to carry out this reaction at the reflux temperature of the solvent, since in general less ammonia will be required to saturate the solvent when elevated temperatures are employed. Usually, only minor molar amounts of ammonia are required to effect a successful performance of the desired reaction of a compound of the formula II above with hexamethylenetetramine. Thus, in a preferred aspect, a solvent is selected which will solubilize the starting materials but will become supersaturated with ammonia when relatively minor molar amounts of it are added thereto.

For example, in one preferred embodiment, ethanol is utilized. It is saturated when about a 1% molar quantity of ammonia is present in the reaction zone; such percentile being determined by a ratio, the numerator of which is the molar amount of ammonia required to supersaturate the solvent medium and the denominator of which is the sum of the molar amounts of hexamethylenetetramine, a compound of the formula II and ammonia present in the reaction zone. The solubility of ammonia in any inert organic solvent useable for the purposes of the present invention can be easily determined by reference to conventional texts. From this determination, the appropriate inert organic solvents can be readily ascertained. The use of pressure, as is noted above, will increase the concentration of ammonia present in the reaction zone over that required to normally saturate the inert organic solvent. Thus, in one aspect, the reaction is performed under a pressure of from about 1 to about 2 atms. Higher amounts of ammonia can be provided to the reaction zone by the simple expedient of using appropriate aqueous inert organic solvents.

As should be apparent from the above, the invention resides in adding ammonia to a reaction medium in which hexamethylenetetramine and a compound of the formula II are to be present. The manner of adding ammonia to the reaction zone is not critical. However, ammonia must be present before both hexamethylenetetramine and a compound of the formula II are present in the reaction zone. Thus, the hexamethylenetetramine can be added to an inert organic solvent of the type referred to above and the ammonia can then be added to the reaction zone prior to the addition of the compound of a formula II above. Alternatively, the ammonia can be dissolved in an inert organic solvent and subsequently a compound of the formula II above and hexamethylenetetramine can be added to the reaction zone.

Furthermore, the manner by which ammonia is introduced into the reaction zone is not critical. In one preferred process aspect, ammonia is provided to the reaction zone simply by bubbling gaseous ammonia therethrough. The ammonia can also be provided to the reaction zone in a less preferred embodiment by utilizing an ammonia generating reagent, e.g. ammonium carbonate which dissociates into ammonia when present in a solvent medium such as ethanol which is heated to reflux. Yields are not usually as good when an ammonia generating reagent is utilized instead of ammonia per se.

A particularly noteworthy feature of the process of the present invention resides in the fact that large molar excesses of hexamethylenetetramine are not required for a successful performance thereof. For example, by the present invention, for every one mole of the starting material of the formula II utilized, if as little as 0.10 moles is utilized, most preferably, if as little as 0.50 moles of hexamethylenetetramine is utilized, the desired compound of the formula I above is obtained. Thus, the present invention achieves an additional and particularly surprising and noteworthy end in that the amount of hexamethylenetetramine utilized is minimized and as a consequence of this, the cost of raw materials utilized in performing the process described herein is reduced without a corresponding diminution of yield. This particularly salient feature of the present invention therefore further provides a particularly commercially viable process. It should be noted that yields do begin to diminish when less than 0.50 moles of hexamethylenetetramine are utilized. However, when 0.50 moles of hexamethylenetetramine are utilized, the desired compound of the formula I is obtained in very good yields and of high quality.

It has been observed that when performing the process of the present invention with hexamethylenetetramine, there is obtained an intermediate of the formula

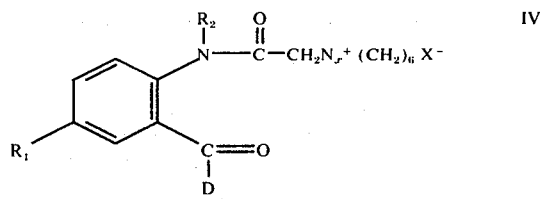

wherein $R_1$, $R_2$, X and D are above. This reaction product can be reacted with ammonia with or without isolation from the reaction medium in which it is prepared to obtain the desired compound of the formula I above.

Thus, a compound of the formula IV, particularly wherein $R_2$ is lower alkyl can be isolated from the reaction medium containing the reaction product of hexamethylenetetramine with a compound of the formula II and the so-obtained compound of the formula IV can be isolated and treated with ammonia whereby to obtain the corresponding compound of the formula I. Alternatively, a compound of the formula II above and hexamethylenetetramine can be added to a reaction medium and there can be provided ammonia thereto without isolating a compound of the formula IV. In a preferred embodiment, the intermediate of the formula IV is not isolated but is reacted with ammonia without isolation from the reaction medium in which it is prepared. This is particularly true when $R_2$ in formula IV above is hydrogen.

A compound of the formula IV can be prepared by techniques other than that described herein. For example, as in the *Journal of Heterocyclic Chemistry* article identified above, a compound of the formula II above can be added to a solvent of low polarity such as acetonitrile with stirring at room temperature. A compound of the formula IV above can be isolated. The so-obtained compound of the formula IV after isolation from the solvent in which it is prepared, can be reacted with ammonia whereby a compound of the formula I above results in good yields and of high purity. The reaction of a compound of the formula IV with ammonia proceeds under the same reaction conditions as ascribed hereinabove to the preparation of a compound of the formula I via the treatment of a compound of the formula II with hexamethylenetetramine and ammonia as should be obvious to one of ordinary skill in the art. Thus, all of the reaction conditions and solvents specified above in connection with the preparation of a compound of the formula I with the use of hexamethylenetetramine apply with equal efficacy to the treatment of the intermediate of the formula IV with ammonia, except that hexamethylenetetramine is not added to the reaction zone.

When following the preparative procedure described above, particularly when utilizing a starting material of the formula II wherein $R_2$ is hydrogen, it has been observed that the reaction of hexamethylenetetramine with the aforementioned compound of the formula II results in the evolution of formaldehyde. The ammonia that is present reacts with the formaldehyde so-formed to regenerate hexamethylenetetramine.

It was further discovered by the present inventors that the desired compound of the formula I can be prepared by treating a compound of the formula II with formaldehyde in the presence of excess ammonia.

In the last-mentioned reaction, there can be utilized anhydrous formaldehyde (paraformaldehyde) or aqueous formaldehyde (38% formalin). Temperature and pressure are not critical to a successful performance of this process but it is preferred to perform the reaction at elevated temperatures, e.g. at about the reflux temperature of the reaction medium. The reaction is preferably effected in the presence of an inert organic solvent and among the many suitable organic solvents, there can be included those identified above in connection with the formation of a compound of the formula I from a compound of the formula II with hexamethylene and ammonia. Therefore, among the many inert organic solvents suitable for the purposes of the present invention, there can be included methanol, ethanol, n-butanol and the like, dimethylformamide and similar inert organic solvents as well as aqueous mixtures of these, e.g. aqueous ethanol or methanol. Here again all that is required of the solvent is that the starting materials be soluble therein and that the solvent does not interfere with the ensuing reaction. Preferred is methanol and/or ethanol.

It can be stated therefore that in this process aspect, the formaldehyde reacts with ammonia which is present in molar excessive amounts to form hexamethylenetetramine whereby a compound of the formula IV results which with or without isolation, preferably without isolation, is converted into a compound of the formula I. The manner in which ammonia is introduced and the amount introduced is the same as described above when a compound of the formula I is prepared utilizing hexamethylenetetramine and ammonia. Thus, in a preferred aspect, the reaction solvent in this process variation is saturated with ammonia, preferably simply by bubbling ammonia through the reaction solvent.

This application is a continuation-in-part of application Ser. No. 282,217 filed Aug. 21, 1972.

The following examples are illustrative but do not limit the present invention. All temperatures are stated in degrees Centigrade.

EXAMPLE 1

To a 2 liter, 4-necked flask equipped with a stirrer, reflux condenser and an inlet for ammonia, there was added 600 ml. of ethanol and 31.7 gm. of hexamethylenetetramine. Ammonia was then bubbled through the resultant reaction medium with stirring until the medium was saturated with ammonia. The saturated solution was heated to reflux, while continuing the bubbling of ammonia through the reaction medium. Thereafter, 78 gm. of 2-bromo-2'-(2-fluorobenzoyl)-4'-nitroacetanilide was carefully added over a period of two hours while maintaining refluxing conditions. The reaction mixture was refluxed for three hours longer and then was concentrated in vacuo to dryness at 50° C. To the residue there was added 300 ml. of toluene and 0.4 gm. of p-toluene sulfonic acid. The resultant medium was heated to reflux for 1 hour. The mixture was then cooled to about 70° C. and washed with water. The toluene layer was then permitted to cool to room temperature. 7-Nitro-5-(2-fluorophenyl)-3H-1,4-benzodiazepin-2-(1H)-one crystallized out. It was isolated by filtration, then washed with toluene and dried.

EXAMPLE 2

To a 2-liter, 4-necked flask equipped with a stirrer, reflux condenser and inlet for ammonia, there was added 600 ml. of ethanol and 31.2 gm. of hexamethylenetetramine. With agitation, ammonia was bubbled through the resultant reaction medium until the ethanol was saturated with ammonia. The resultant medium was heated to reflux. While maintaining the reaction under refluxing conditions and bubbling ammonia therethrough, there was carefully added 40 gm. of 2-bromo-4'-chloro-2'-(2-chlorobenzoyl)acetanilide over a period of two hours. The reaction mixture so obtained was then evaporated to dryness. To the residue, there was added 300 ml. of toluene and then 0.3 gm. of para-toluene sulfonic acid. The toluene solution was heated to reflux. The reaction medium was permitted to cool to 70° C. After cooling, it was washed with hot water. The toluene extract was permitted to cool to room temperature. After cooling to 10° C., the crystalline product which formed was filtered off, washed with toluene and petroleum ether, dried overnight under vacuum at 100° to give 7-chloro-5-(2-chlorophenyl)-1,3-dihydro-2H-1,4-benzodiazpin-2-one, m.p. 200°–200.5° C.

EXAMPLE 3

To a 2-liter, 4-necked flask equipped with a reflux condenser, an ammonia addition tube and a stirrer, there was added 600 ml. of ethanol and 30.4 gm. of hexamethylenetetramine. Ammonia was bubbled through the reaction medium until the ethanol became supersaturated. The reaction mixture was heated to reflux while 40 gm. of 2-bromo-2'-(2-chlorobenzoyl)-4'-nitroacetanilide was carefully added to the resultant medium over a period of 3½ hours. The refluxing and bubbling of ammonia through the reaction medium was continued for three hours longer and then it was evaporated to dryness. To the residue was added 250 ml. of toluene and 0.4 gm. of para-toluene sulfonic acid. The mixture was refluxed for 1 hour. The toluene layer was cooled to 70° C. The resultant medium was washed with water. The toluene layer was then cooled to room temperature. The product crystallizes from the reaction medium. The crystals were filtered off, and washed once with toluene and once with petroleum ether and dried, yielding 5-(2-chlorophenyl)-1,3-dihydro-7-nitro-2H-1,4-benzodiazepin-2-one, m.p. 203°–204° C.

EXAMPLE 4

Into a 12-liter, 3-necked flask equipped with a condenser and an ammonia addition tube, there was added 7.2 liters of ethanol and 470.4 gm. of hexamethylenetetramine. The ammonia was bubbled through the resultant reaction medium with stirring until the medium become supersaturated. With refluxing, 480.0 gm. of 2-chloroacetamido-5-chlorobenzophenone was carefully added over a period of 4 hours. The resultant mixture was heated at reflux for an additional 2 hours while bubbling ammonia there through. The resultant medium was then left to stand overnight and then concentrated to dryness in vacuo. To the concentrate was added 2.4 liters of toluene and the resultant medium was heated to reflux. 0.5 Gm. of para-toluene sulfonic acid was then added. The refluxing was continued for a period of one hour. After cooling the medium to 70° C., 1.5 liters of hot water was added. The product which separated was cooled to 20° and isolated by filtration, washed and dried in vacuo. The product obtained was 7-chloro-1,3-dihydro-5-phenyl-2H-1,4-benzodiazepin-2-one.

In a similar manner as described above, there can be prepared 7-bromo-1,3-dihydro-5-(2-pyridyl)-2H-1,4-benzodiazepin-2-one melting at 225°–235° C. from 2-(2-chloroacetamido-5-bromo benzoyl)pyridine.

EXAMPLE 5

A 12-liter, 3-neck flask equipped with a sealed stirrer, reflux condenser, and ammonia addition tube is charged with 7.2 liters of ethanol. The alcohol is heated to reflux with stirring on a steam bath. The solvent is then saturated with ammonia to a concentration of about 0.6 to 0.7% by weight. While the heating bath is momentarily removed, 493 grams of hexamethylenetetramine is added. Heating is resumed, and 480 grams of 2-chloroacetamido-5-chlorobenzophenone, is slowly added in small increments. Ammonia is steadily bubbled into the refluxing solution. The addition of the chloroacetamido compound is done over a 3 to 4-hour period. The reaction mixture is the heated under reflux for an additional 2 hours. The flow of ammonia is interrupted and the alcohol is removed by vacuum distillation.

The reaction flask is transferred to a heating mantle and the residue is slurried and heated to reflux in 2.4 liters of toluene. At reflux temperature, 2 × 0.5 grams of p-toluenesulfonic acid is added about 15 minutes apart. A small amount of water (ca. 1 to 2 ml.) separates. The slurry of crystals is then cooled to 70° C. and the water-soluble material is dissolved by the addition of 1.5 liters of hot (70° C.) water. The heterogenous mixture is stirred overnight while cooling to room temperature. 7-Chloro-1,3-dihydro-5-phenyl-2H-1,4-benzodiazepin-2-one which separates is isolated by filtration and washed once with 250 ml. of cold tap water and once with 250 ml. of cold (0° C.) toluene. The product is then dried to constant weight at 80° C.

EXAMPLE 6

To a 2-liter, 4-necked flask equipped with a stirrer, a reflux condenser and an ammonia tube, there was added 600 ml. of ethanol and 37.9 g. of hexamethylenetetramine with stirring. Ammonia was bubbled through the resultant reaction medium with stirring until reflux temperature was reached. Then there was carefully added to the refluxing solution 40.0 g. of 2-chloroacetamido-5-nitro benzophenone. Ammonia is steadily bubbled into the reaction mixture while continuing to reflux for three hours. The resultant solution was cooled, evaporated to dryness at 50° C. The residue was dissolved in 300 ml. of toluene. 0.3 G. of paratoluene sulfonic acid was added to the resultant solution. The solution was heated to reflux. The refluxing was continued for 1 hour. The reaction medium was then permitted to cool to room temperature. The product which separated was filtered off, washed with water and dried. This material was taken up in 435 ml. of methylene chloride. It was then filtered through Hyflo. Upon the addition of 90 ml. of 3N nitric acid to the filtrate, crystals appeared. They were filtered off, washed with methylenechloride and dried for 15 minutes. The crystals were added to 1 liter of water with stirring. Ammonium hydroxide was then carefully added to the resultant medium until a pH of about 8 was reached. After stirring the resultant medium for ½ hours, the crystalline precipitate which formed were filtered off, washed with cold water and dried at 80° for 8 hours yielding 1,3-dihydro-7-nitro-5-phenyl-2H-1,4-benzodiazepin-2-one of melting point 217°–219°.

EXAMPLE 7

To 1350 ml. of ethanol there was added 90 gm. of 2-chloroacetamido-5-chlorobenzophenone and 92.5 gm. of hexamethylenetetramine. Ammonia was bubbled through the resultant medium under a pressure. The resultant medium was heated to reflux. The resultant reaction medium was evaporated in vacuum to dryness. It was triturated then with 250 ml. of hot water twice on a steam bath. The aqueous phase was removed by decantation. The crystalline residue was heated for 30 minutes in 250 ml. of toluene on a steam bath and then cooled to room temperature. The crystals which formed were filtered, washed twice with 25 ml. of toluene and 25 ml. of petroleum ether and dried to constant weight yielding 7-chloro-1,3-dihydro-5-phenyl-2H-1,4-benzodiazepin-2-one melting point 213°–215° C.

EXAMPLE 8

13.5 liters of 95% ethanol, 900 gms. of 2-chloroacetamido, 5-chlorobenzophenone and 925 gms. of hexamethylenetetramine were charged to a stirred pressure vessel. The medium was saturated with ammonia gas at ch. 15 # gauge of pressure with stirring. The ammonia supply was turned off. The resultant medium was heated for three hours at 78°–80° C. After cooling and venting the ammonia, the batch was removed from the pressure vessel to a vacuum still. The batch was concentrated to dryness in vacuo from a steam bath. The the residue was added 2½ liters of toluene and 5.0 g. of p-toluenesulfonic acid and the resultant mixture was heated to reflux. Ca. 5 mls. of water formed, removed by azeotropism. After cooling to 70° C. three liters of water at 70° C. were added. The crystal slurry so obtained was cooled for one hour at +10° to +15° C. After filtering, washing the product with 2 × 250 ml. of tap water and once with 250 ml. of cold (+10° C.) toluene and drying to constant weight, 7-chloro-1,3-dihydro-5-phenyl-2H-1,4-benzodiazepin-2-one was obtained.

EXAMPLE 9

A mixture of hexamethylenetetramine (17.5 g., 0.125 mol), methanol (135.5 ml) and 2(2-chloro-N- methylacetamido)-5-chlorobenzophenone (80.5 g., 0.25 mol) was saturated with ammonia. Heat the stirred mixture slowly to reflux with a steady stream of ammonia flowing through the mixture. During the course of the reaction

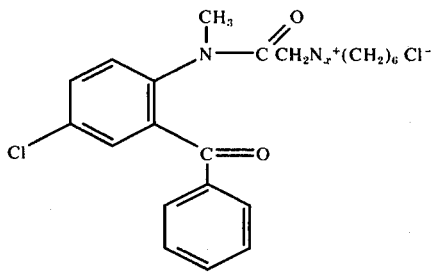

was prepared. The product was not isolated. Hold at reflux for 6 hours. Stop the flow of ammonia and remove the solvent under vacuum. Take up the residue in a mixture of toluene (500 ml.) and hot water (500 ml). Separate the toluene phase and add to it, with stirring, 3N nitric acid (169 ml). The crystals which separate are filtered, wash with toluene (50 mls) and resuspended in a mixture of toluene (250 ml) and water (250 ml). Concentrated ammonia (30 ml) is added to pH 8. The toluene phase is separated, washed with water (250 ml) and then distilled to dryness in vacuo yielding 96.09% of 7-chloro-1-methyl-1,3-dihydro-5-phenyl-2H-1,4-benzodiazepin-2-one, melting point 125° to 127° C.

EXAMPLE 10

A mixture of ethanol (600 ml) and hexamethylenetetramine (39.1 g., 0.279 mol) was stirred and saturated with ammonia. With ammonia bubbling into the mixture it was slowly heated to reflux. Over a period of 4½ hours, 2-(2-chloro-N-methylacetamido)-5-chlorobenzophenone (40 g., 0.124 mol) was added in increments yielding

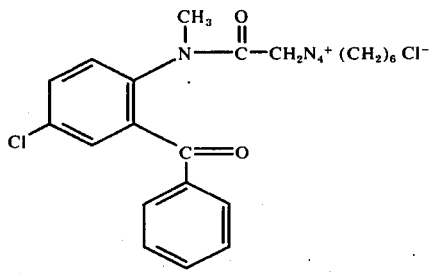

which was not isolated. Refluxing was continued for 2 hours longer. The reaction mixture was then distilled to dryness in vacuo at 50° C. The residue was stirred with toluene (250 ml), heated to reflux and heated with two increments of para-toluene sulfonic acid. Reflux was continued for one hour. After cooling to 70° C., the toluene was washed with hot water to remove soluble salts and distilled to dryness in vacuo. The residue was dissolved in hot ethanol (111 mol) and the solution cooled at −10° C. for one hour. The crystalline 7-chloro-1,3-dihydro-1-methyl-5-phenyl-2H-1,4-benzodiazepin-2-one obtained was isolated and weighed 29 g., melting point 129° to 131° C. Concentration of the mother liquor by ca. 50% gave a second crop weighing 2.0 g. melting at 127° C.

EXAMPLE 11

A mixture of ethanol (1100 ml), hexamethylenetetramine (70.0 g., 0.5 mol), 26% ammonium hydroxide (58 ml) and 2-chloroacetamido-5-chlorobenzophenone (308.2 g., 1.0 mol) was stirred and slowly heated to reflux with ammonia bubbling into the mixture. Reflux was continued for 5 hours, the flow of ammonia was interrupted, and the reaction mixture distilled to dryness in vacuo. The residue was heated to reflux for 30 minutes in a mixture of toluene (500 mls) and water (500 mls) and then allowed to cool slowly to room temperature. The crystalline material was filtered, washed with toluene (100 mls) and hot water (2 × 250 mls) and dried to constant weight. The product, 7-chloro-1,3-dihydro-5-phenyl-2H-1,4-benzodiazepin-2-one (226 g) obtained corresponded to a yield of 83.5%, melting point 210° C.

EXAMPLE 12

A mixture of ethanol (1100 mls), hexamethylenetetramine (35 g., 0.25 mol), 26% ammonium hydroxide (58 ml), and 2-chloroacetamido-5-chlorobenzophenone (308.2 g., 1.0 mol) were permitted to react as described in Example 11 except that the reflux period was increased from 5 to 7 hours. The reaction product, 7-chloro-1,3-dihydro-5-phenyl-2H-1,4-benzodiazepin-2-one (221 g.) isolated in a manner identical with Example 11, was obtained in 81.6% yield, melting point 208.5° to 209° C.

EXAMPLE 13

A mixture of methanol (550 mls), hexamethylenetetramine (14.1 g., 0.1 mol) and 2-chloroacetamido-5-chlorobenzophenone (308.2 g., 1.0 mol) was stirred and saturated with ammonia at room temperature. The mixture was heated slowly to reflux with a steady stream of ammonia bubbling through the solution. Refluxing was continued for 24 hours. The flow of ammonia was interrupted and the crystal slurry obtained was cooled to room temperature. The product, filtered, washed with methanol (2 × 125 ml) and hot water (4 × 500 ml), and dried gave 7-chloro-1,3-dihydro-5-phenyl-2H-1,4-benzodiazepin-2-one (169 g., 62.3%) melting at 213° to 215° C.

EXAMPLE 14

A mixture of ethanol (300 ml) and hexamethylenetetramine (20 g., 0.143 mol) was stirred, heated to reflux, and saturated with ammonia. 2-Chloroacetamidobenzophenone (18.1 g., 0.066 mol) was added in small increments over 3 to 4 hours while a steady stream of ammonia was bubbled into the reaction mixture. Refluxing was continued for 3 hours after complete addition of 2-chloroacetamidobenzophenone. The flow of ammonia was interrupted and the ethanol removed by distillation in vacuo. The residue obtained was taken up in chloroform (200 ml), and washed with water (100 ml) at 50° C. The chloroform layer was evaporated to dryness at 30° C. and the oily solid obtained was recrystallized from toluene (100 ml) to give 1,3-dihydro-5-phenyl-2H-1,4-benzodiazepin-2-one (13.2 g., 86%), melting at 184°–186° C.

EXAMPLE 15

A mixture of methanol (275 ml.) and 2-chloroacetamido-5-chlorobenzophenone (154.2 g., 0.5 mol) was heated to reflux with a steady stream of ammonia bubbling in. At reflux 37% formaldehyde solution (237 ml) was fed in over ca. 40 minutes. The reaction mixture was then heated under reflux for 5 hours. The flow of ammonia was stopped and the slurry of crystals was cooled to room temperature, filtered, washed with methanol (2 × 125 ml), hot water (4 × 500 ml) and dried. There was obtained 7-chloro-1,3-dihydro-5-phenyl-2H-1,4-benzodiazepin-2-one (104.6 g., 77.3%), melting at 211.5° to 214.5° C.

EXAMPLE 16

A mixture of paraformaldehyde (147.2 g.) and methanol (550 ml.) was stirred and heated to reflux with a steady stream of ammonia bubbling in. The crystal slurry of hexamethylenetetramine which formed was cooled to room temperature and 2-chloroacetamido-5-chlorobenzophenone (308.2 g., 1.0 mol) was added in one portion. With ammonia bubbling in, the reaction mixture was heated at reflux for 10 hours. The flow of ammonia was interrupted and the reaction mixture was cooled to room temperature, filtered, washed with methanol (2 × 125 ml.) and hot water (4 × 500 ml) and dried. There was obtained 7-chloro-1,3-dihydro-5-phenyl-2H-1,4-benzodiazepin-2-one (220.4 g., 81.4%) melting at 212.5° to 215° C.

EXAMPLE 17

Paraformaldehyde (200 g., 91% flake) is placed in a stirred reactor equipped with a reflux condenser, decanter, and ammonia addition tube. Methanol (575 mls.) is added and then gaseous ammonia below the surface of the reaction mixture. 2-Chloroacetamidobenzophenone (273.7 g.) is then added. With a slow, continuous flow of ammonia to the reaction zone, the mixture is heated at reflux for 5 hours. The crystal slurry obtained is distilled to recover the methanol. Toluene (1350 mls.) is now added to the crystal residue and residual water is removed by azeotropic distillation through the decanter. When dry, the hot toluene solution is filtered, the filtrate is cooled for crystallization, and the product obtained isolated to give 1,3-dihydro-5-phenyl-2H-1,4-benzodiazepin-2-one (200 g., 84.7%) m.p. 180°–181° C. (uncorr.).

EXAMPLE 18

Paraformaldehyde (147.2 g., 91% flake) is placed in a stirred reactor equipped with an ammonia addition tube and a reflux condenser. Methanol (550 mls.) is added, along with 2-chloroacetamido-5-chloro-2'-fluorobenzophenone (326.2 g.) at room temperature. The reaction mixture is stirred and ammonia gas bubbled in below the surface of the reaction mixture. The reaction mixture was then heated at reflux for 10 hours with a steady flow of ammonia gas. Cool to room temperature and filter the crystalline product obtained. Wash product with cold methanol (2 × 125 mls. at −10° C.), followed by hot water (4 × 500 mls at 60° C.). When dry, there was obtained 7-chloro-1,3-dihydro-5-(2-fluorophenyl)-2H-1,4-benzodiazepin-2-one (205 g., 71%) m.p. 205.5°–207° C. (uncorr.).

EXAMPLE 19

250 g. of 2-chloroacetamido-5-chlorobenzophenone, 122.5 g. of hexamethylenetetramine were added to 2.5 liters of acetonitrile in a 5 l., 3-neck flask, equipped with a stirrer and calcium chloride drying tube. The reactants were stirred for 72 hrs. at room temperature. All reactants went into solution. The product which was

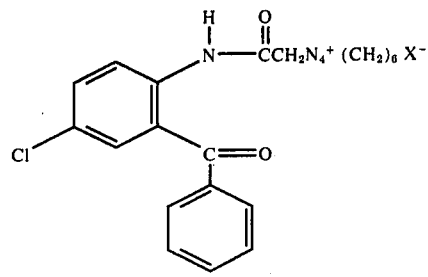

crystallized out. The product was filtered, washed with a small amount of fresh solvent and dried yielding 328 gms. or 91.4% (crude yield) of product, m.p. 169°–170° C.

EXAMPLE 20

89.7 gms. of product obtained in Example 19 was dissolved in ammonia ethanol. The so-obtained reaction mixture was heated and gaseous ammonia was bubbled into the reaction mixture continuously during the heat-up and for a 5-hour period of reflux yielding 7-chloro-1,3-dihydro-5-phenyl-2H-1,4-benzodiazepin-2-one which was isolated according to conventional procedures. Yield, 86.6%, m.p. 212°–214° C.

EXAMPLE 21

In a one liter, stirred flask equipped with a reflux condenser was placed 89.7 gms. of

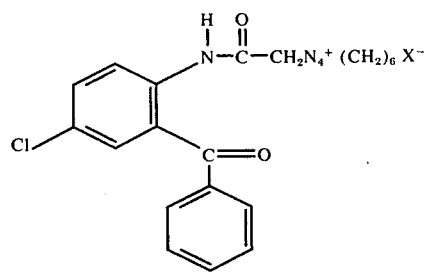

61.6 gms. of 2-chloroacetamido-5-chlorobenzophenone, 22.4 mls. of 26% ammonium hydroxide and 425 mls. of ethanol. Ammonia was bubbled into the reaction mixture while it was stirred and heated to reflux. Refluxing was continued for 5 hrs. thereafter with stirring. The reaction mixture was distilled to dryness in a Swissco evaporator. The residue was then heated at reflux for one hour in a mixture of 100 mls. of toluene and 100 mls. of water and cooled to room temperature yielding 7-chloro-1,3-dihydro-5-phenyl-2H-1,4-benzodiazepin-2-one. The product was filtered, washed with 20 mls. of water and 20 mls. of toluene and dried. It weighed 92.5 gms. or 85.4%. The crude product melted at 210°–213° C.

I claim:
1. A process for preparing a compound of the formula

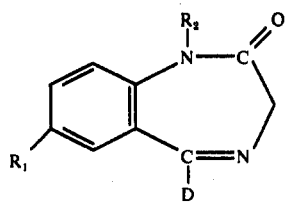

wherein D is selected from the group consisting of

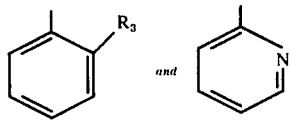

$R_1$ is selected from the group consisting of hydrogen, halogen, nitro and trifluoromethyl; $R_2$ is selected from the group consisting of hydrogen and lower alkyl; and $R_3$ is selected from the group consisting of hydrogen and halogen
which comprises reacting a compound of the formula

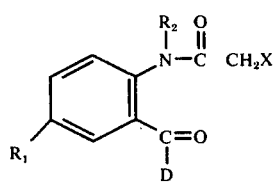

wherein D, $R_1$ and $R_2$ are as above and X is selected from the group consisting of chlorine, bromine and iodine
with hexamethylenetetramine in the presence of ammonia and an inert organic solvent.

2. A process as defined in claim 1 wherein the reaction is effected under pressure.

3. A process as defined in claim 1 wherein the ammonia is provided to the reaction zone in such quantities as to saturate the inert organic solvent being employed.

4. A process as defined in claim 1 wherein D is the grouping

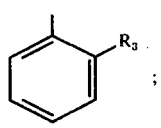

$R_1$ is halogen or nitro and $R_2$ is hydrogen or methyl.

5. A process as defined in claim 4 wherein $R_1$ is chlorine, bromine or nitro, $R_2$ is hydrogen or methyl, and $R_3$ is hydrogen, chlorine or fluorine.

6. A process as defined in claim 5 wherein the ammonia is provided to the reaction zone in such quantities as to saturate the inert solvent being employed.

7. A process as defined in claim 6 wherein $R_1$ is nitro.

8. A process as defined in claim 6 wherein $R_1$ is chlorine.

9. A process as defined in claim 1 wherein $R_1$ is chlorine, $R_2$ is hydrogen and D is the grouping

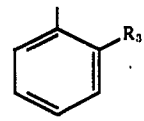

wherein $R_3$ is hydrogen.

10. A process as defined in claim 9 wherein the ammonia is provided to the reaction zone in such quantities as to saturate the inert organic solvent being employed.

11. A process as in claim 10 wherein an aqueous inert organic solvent is utilized.

12. A process for preparing a compound of the formula

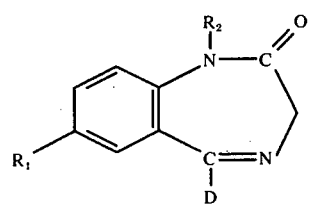

wherein D is selected from the group consisting of

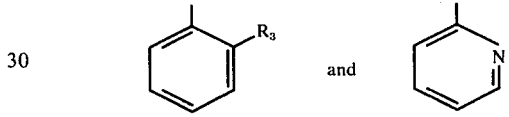

$R_1$ is selected from the group consisting of hydrogen, halogen, nitro and trifluoromethyl; $R_2$ is selected from the group consisting of hydrogen and lower alkyl; and $R_3$ is selected from the group consisting of hydrogen and halogen
which comprises reacting a compound of the formula

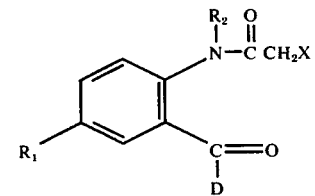

wherein D, $R_1$ and $R_2$ are as above and X is selected from the group consisting of chlorine, bromine and iodine
with formaldehyde in the presence of ammonia and an inert organic solvent.

13. A process as in claim 12 wherein X is chlorine.

14. A process as defined in claim 13 wherein D is the grouping

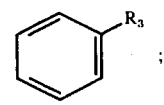

$R_1$ is halogen or nitro and $R_2$ is hydrogen or methyl.

15. A process as defined in claim 14 wherein $R_1$ is chlorine, bromine or nitro, $R_3$ is hydrogen or methyl, and $R_4$ is hydrogen, chlorine or fluorine.

16. A process as defined in claim 15 wherein $R_1$ is chlorine.

* * * * *